US008128652B2

(12) United States Patent
Paprocki

(10) Patent No.: US 8,128,652 B2
(45) Date of Patent: Mar. 6, 2012

(54) METHOD AND APPARATUS FOR SEALING AN INTERNAL TISSUE PUNCTURE INCORPORATING A BLOCK AND TACKLE

(75) Inventor: Loran Paprocki, St. Louis Park, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 1605 days.

(21) Appl. No.: 10/712,539

(22) Filed: Nov. 13, 2003

(65) Prior Publication Data
US 2005/0107827 A1 May 19, 2005

(51) Int. Cl.
*A61B 17/03* (2006.01)
(52) U.S. Cl. .......................... 606/213; 606/232
(58) Field of Classification Search .......... 606/213–218, 606/232
See application file for complete search history.

(56) References Cited

U.S. PATENT DOCUMENTS

| | | | |
|---|---|---|---|
| 4,317,445 A | 3/1982 | Robinson | |
| 4,744,364 A | 5/1988 | Kensey | |
| 4,890,612 A * | 1/1990 | Kensey | 606/213 |
| 5,021,059 A * | 6/1991 | Kensey et al. | 606/213 |
| 5,061,274 A * | 10/1991 | Kensey | 606/213 |
| 5,108,421 A | 4/1992 | Fowler | |
| 5,192,302 A * | 3/1993 | Kensey et al. | 606/213 |
| 5,222,974 A | 6/1993 | Kensey | 606/213 |
| 5,282,827 A * | 2/1994 | Kensey et al. | 606/215 |
| 5,290,310 A | 3/1994 | Makower et al. | |
| 5,292,327 A | 3/1994 | Dodd et al. | |
| 5,292,332 A | 3/1994 | Lee | |
| 5,304,184 A | 4/1994 | Hathaway et al. | |
| 5,306,254 A | 4/1994 | Nash et al. | |
| 5,312,435 A * | 5/1994 | Nash et al. | 606/213 |
| 5,320,639 A | 6/1994 | Rudnick | |
| 5,324,298 A | 6/1994 | Phillips et al. | |
| 5,326,350 A | 7/1994 | Li | |
| 5,334,216 A | 8/1994 | Vidal et al. | |
| 5,342,393 A | 8/1994 | Stack | |
| 5,368,601 A | 11/1994 | Sauer et al. | |
| 5,383,896 A | 1/1995 | Gershony et al. | |
| 5,383,897 A | 1/1995 | Wholey | |
| 5,383,899 A | 1/1995 | Hammerslag | |
| RE34,866 E | 2/1995 | Kensey et al. | |
| 5,391,183 A | 2/1995 | Janzen et al. | |
| 5,397,326 A | 3/1995 | Mangum | |
| 5,403,328 A | 4/1995 | Shallman | |
| 5,403,329 A | 4/1995 | Hinchcliffe | 606/147 |
| 5,405,354 A | 4/1995 | Sarrett | |
| 5,411,520 A * | 5/1995 | Nash et al. | 606/213 |
| 5,417,699 A | 5/1995 | Klein et al. | |

(Continued)

*Primary Examiner* — Darwin Erezo
(74) *Attorney, Agent, or Firm* — Holland & Hart

(57) ABSTRACT

A sealing device incorporating a block and tackle for assisting in sealing an internal tissue puncture with an internal and external component. The block and tackle provides a mechanical advantage multiplying an initial force to facilitate compression of the internal and external component together across the internal tissue puncture. The internal and external components may be an anchor and collagen sponge, respectively. The internal tissue puncture is generally an arteriotomy intentionally created in order to perform a vascular procedure. The ability to exert a greater compression force across the arteriotomy eliminates a tamping tube common to prior internal tissue puncture closure devices, and also eliminates additional steps heretofore common to sealing internal tissue punctures. The steps eliminated by application of the principles described herein include tamping the collagen sponge, attaching a tamping spring between a tamping tube and a filament connecting the anchor to the collagen sponge, and later removing the tamping spring.

35 Claims, 6 Drawing Sheets

U.S. PATENT DOCUMENTS

| | | | |
|---|---|---|---|
| 5,423,837 A | 6/1995 | Mericle et al. | |
| 5,431,639 A | 7/1995 | Shaw | |
| 5,431,666 A | 7/1995 | Sauer et al. | |
| 5,437,631 A | 8/1995 | Janzen | |
| 5,441,517 A * | 8/1995 | Kensey et al. | 606/213 |
| 5,443,481 A | 8/1995 | Lee | |
| 5,454,821 A | 10/1995 | Harm et al. | |
| 5,462,561 A | 10/1995 | Voda | |
| 5,486,195 A | 1/1996 | Myers et al. | |
| 5,496,332 A | 3/1996 | Sierra et al. | |
| 5,496,335 A | 3/1996 | Thomason et al. | |
| 5,507,744 A | 4/1996 | Tay et al. | |
| 5,507,758 A | 4/1996 | Thomason et al. | |
| 5,527,322 A | 6/1996 | Klein et al. | |
| 5,531,759 A * | 7/1996 | Kensey et al. | 606/213 |
| 5,545,178 A * | 8/1996 | Kensey et al. | 606/213 |
| 5,549,618 A | 8/1996 | Fleenor et al. | |
| 5,549,633 A * | 8/1996 | Evans et al. | 606/139 |
| 5,571,181 A | 11/1996 | Li | |
| 5,584,861 A | 12/1996 | Swain et al. | |
| 5,591,205 A | 1/1997 | Fowler | |
| 5,593,422 A | 1/1997 | Muijs Van de Moer et al. | |
| 5,601,603 A | 2/1997 | Illi | |
| 5,613,974 A | 3/1997 | Andreas et al. | |
| 5,620,461 A | 4/1997 | Muijs Van De Moer et al. | |
| 5,626,601 A | 5/1997 | Gershony et al. | |
| 5,643,318 A | 7/1997 | Tsukernik et al. | |
| 5,645,566 A | 7/1997 | Brenneman et al. | |
| 5,649,959 A | 7/1997 | Hannam et al. | |
| 5,653,719 A | 8/1997 | Raiken | |
| 5,653,730 A | 8/1997 | Hammerslag | |
| 5,662,681 A | 9/1997 | Nash | 606/213 |
| 5,665,106 A | 9/1997 | Hammerslag | |
| 5,674,231 A | 10/1997 | Green et al. | |
| 5,676,689 A * | 10/1997 | Kensey et al. | 606/213 |
| 5,681,334 A * | 10/1997 | Evans et al. | 606/148 |
| 5,700,277 A * | 12/1997 | Nash et al. | 606/213 |
| 5,707,393 A * | 1/1998 | Kensey et al. | 606/213 |
| 5,725,498 A | 3/1998 | Janzen et al. | |
| 5,725,551 A | 3/1998 | Myers et al. | |
| 5,728,114 A * | 3/1998 | Evans et al. | 606/148 |
| 5,728,122 A | 3/1998 | Leschinsky et al. | |
| 5,728,132 A | 3/1998 | Van Tassel et al. | |
| 5,728,133 A | 3/1998 | Kontos | |
| 5,728,134 A | 3/1998 | Barak | |
| 5,741,223 A | 4/1998 | Janzen et al. | |
| 5,746,755 A | 5/1998 | Wood et al. | |
| 5,755,727 A | 5/1998 | Kontos | |
| 5,759,194 A | 6/1998 | Hammerslag | |
| 5,766,183 A | 6/1998 | Sauer | |
| 5,766,206 A | 6/1998 | Wijkamp et al. | |
| 5,769,862 A | 6/1998 | Kammerer et al. | |
| 5,782,861 A | 7/1998 | Cragg et al. | |
| 5,792,173 A | 8/1998 | Breen et al. | |
| 5,810,810 A | 9/1998 | Tay et al. | |
| 5,810,846 A | 9/1998 | Virnich et al. | |
| 5,810,884 A | 9/1998 | Kim | |
| 5,814,065 A | 9/1998 | Diaz | |
| 5,820,631 A | 10/1998 | Nobles | |
| 5,827,299 A | 10/1998 | Thomason et al. | |
| 5,830,130 A | 11/1998 | Janzen et al. | |
| 5,843,124 A | 12/1998 | Hammerslag | |
| 5,853,421 A | 12/1998 | Leschinsky et al. | |
| 5,855,559 A | 1/1999 | Van Tassel et al. | |
| 5,855,585 A | 1/1999 | Kontos | |
| 5,860,990 A | 1/1999 | Nobles et al. | |
| 5,860,991 A | 1/1999 | Klein | 606/144 |
| 5,861,004 A | 1/1999 | Kensey | 606/213 |
| 5,861,005 A | 1/1999 | Kontos | |
| 5,868,762 A | 2/1999 | Cragg et al. | |
| 5,876,411 A | 3/1999 | Kontos | |
| 5,902,311 A | 5/1999 | Andreas et al. | |
| 5,906,631 A | 5/1999 | Imran | |
| 5,910,155 A | 6/1999 | Ratcliff et al. | |
| 5,919,207 A | 7/1999 | Taheri | |
| 5,935,147 A | 8/1999 | Kensey | 606/213 |
| 5,941,897 A | 8/1999 | Myers | |
| 5,957,952 A | 9/1999 | Gershony et al. | |
| 5,964,782 A | 10/1999 | Lafontaine et al. | |
| 5,976,161 A | 11/1999 | Kirsch et al. | |
| 5,980,539 A | 11/1999 | Kontos | |
| 5,997,555 A | 12/1999 | Kontos | |
| 6,007,562 A | 12/1999 | Harren et al. | |
| 6,007,563 A * | 12/1999 | Nash et al. | 606/213 |
| 6,017,359 A | 1/2000 | Gershony et al. | |
| 6,024,747 A | 2/2000 | Kontos | |
| 6,033,401 A | 3/2000 | Edwards et al. | |
| 6,033,427 A | 3/2000 | Lee | |
| 6,036,721 A | 3/2000 | Harren et al. | |
| 6,042,601 A | 3/2000 | Smith | 606/232 |
| 6,045,569 A | 4/2000 | Kensey et al. | |
| 6,048,357 A | 4/2000 | Kontos | |
| 6,048,358 A | 4/2000 | Barak | |
| 6,063,085 A | 5/2000 | Tay et al. | |
| 6,071,300 A | 6/2000 | Brenneman et al. | |
| 6,077,279 A | 6/2000 | Kontos | |
| 6,090,130 A | 7/2000 | Nash | 606/213 |
| 6,110,184 A | 8/2000 | Weadock | |
| 6,120,524 A | 9/2000 | Taheri | |
| 6,126,675 A | 10/2000 | Shchervinsky et al. | |
| 6,132,439 A | 10/2000 | Kontos | |
| 6,136,010 A | 10/2000 | Modesitt et al. | |
| 6,139,556 A | 10/2000 | Kontos | |
| 6,162,192 A | 12/2000 | Cragg et al. | |
| 6,171,317 B1 | 1/2001 | Jackson | 606/148 |
| 6,174,322 B1 | 1/2001 | Schneidt | |
| 6,179,863 B1 | 1/2001 | Kensey et al. | 606/215 |
| 6,183,496 B1 | 2/2001 | Urbanski | |
| 6,193,670 B1 | 2/2001 | Van Tassel et al. | |
| 6,197,042 B1 | 3/2001 | Ginn et al. | |
| 6,206,895 B1 | 3/2001 | Levinson | |
| 6,231,561 B1 | 5/2001 | Frazier et al. | |
| 6,245,080 B1 | 6/2001 | Levinson | |
| 6,350,280 B1 * | 2/2002 | Nash et al. | 623/1.36 |
| 6,398,796 B2 | 6/2002 | Levinson | |
| 6,425,911 B1 | 7/2002 | Akerfeldt et al. | |
| 6,425,924 B1 | 7/2002 | Rousseau | |
| 6,508,828 B1 | 1/2003 | Akerfeldt et al. | |
| 6,547,806 B1 | 4/2003 | Ding | |
| 6,569,185 B2 | 5/2003 | Ungs | |
| 6,596,012 B2 | 7/2003 | Akerfeldt et al. | |
| 6,596,014 B2 | 7/2003 | Levinson et al. | |
| 6,682,489 B2 | 1/2004 | Tenerz et al. | |
| 6,712,837 B2 | 3/2004 | Akerfeldt et al. | |
| 6,860,895 B1 | 3/2005 | Akerfeldt et al. | |

* cited by examiner

METHOD AND APPARATUS FOR SEALING AN INTERNAL TISSUE PUNCTURE INCORPORATING A BLOCK AND TACKLE

TECHNICAL FIELD

This invention relates to medical devices, and more particularly to a method and apparatus for sealing internal incisions or punctures utilizing a block and tackle.

BACKGROUND OF THE INVENTION

Medical science has advanced tremendously in the last century to include the use of numerous complex internal procedures to treat various human conditions. Many of these procedures require a surgeon to puncture or slice into a portion of the internal human anatomy in order to perform a particular process. For example, many cardiology procedures require accessing the internal portion of a corporeal vessel. After a procedure is completed, the surgeon must repair damage to the internal organ or vessel in order for the patient to properly recover. While it is possible to suture or seal the skin and other large organs after the procedure, it is not always possible to suture delicate vessels with the same technique. Therefore, new techniques have been developed to seal punctures and incisions in delicate vessels such as arteries and veins.

One device currently used to seal punctures in delicate vessels in a quick and efficient manner so as to minimize the recovery time of patients undergoing these types of procedures is the Angio-Seal®. The Angio-Seal® is commonly used to seal arteriotomys including those created when the femoral artery is deliberately punctured in order to perform a vascular procedure. The femoral artery is often punctured in order to clear blockages or obstructions in the patient's circulatory system. Examples of the Angio-Seal® are disclosed by U.S. Pat. Nos. 5,282,827 and 5,662,681, which are hereby incorporated by reference. These patents describe certain embodiments of Angio-Seal® devices and procedures for sealing an arteriotomy or other internal punctures and incisions.

As described more fully in the aforementioned patents, when an Angio-Seal® is used, an anchor is most often inserted through an arteriotomy and positioned against an interior wall of an artery. A collagen sponge is positioned at an exterior wall of the artery above the arteriotomy. The anchor and collagen sponge are then sandwiched or compressed together to facilitate rapid hemostasis and sealing of the arteriotomy.

The process of sandwiching the anchor and the collagen sponge together is initially performed manually by pushing a tamping tube distally while exerting a proximal force on a suture extending from the Angio-Seal® device to the collagen sponge and anchor. A tamping spring is then attached to the distal end of the suture between the tamper tube and a crimp stop on the suture so as to maintain opposing forces on the suture and the tamping tube. Unfortunately, the extra step of attaching the tamping spring to the suture further complicates the procedure and requires the use of the extra external spring component, which may be misplaced or misused during the surgery. Surgeons often perform extremely complex procedures and it is important to simplify devices as much as possible so as to allow them to concentrate on patient care, and not on extraneous components. In addition, a faster method of sealing an incision generally translates into less blood loss for the patient. Therefore, there is a need in the industry for a device that is capable of simplifying the process of tamping or sandwiching an internal and external component together in a tissue puncture sealing device such as an Angio-Seal® device.

SUMMARY OF EMBODIMENTS OF THE INVENTION

The issues raised above and others are addressed by embodiments of the present invention, which is directed to a tissue puncture closure assembly incorporating a block and tackle for assisting in sealing an internal incision with an internal and external component. The assembly may include a puncture closure device and an insertion sheath. The block and tackle provides a mechanical advantage for sandwiching the internal and external components together across the internal incision. The internal and external components of the puncture closure device may be an anchor and collagen sponge, respectively. Likewise, the internal incision is generally an arteriotomy intentionally created in order to perform a vascular procedure. The addition of the block and tackle provides a greater compression force at the arteriotomy than previously available and eliminates the steps of tamping the collagen sponge with a tamping tube, attaching a tamping spring to the suture in order to exert a continuous pressure between the anchor and collagen sponge, and later removing the tamping spring.

One embodiment of the present invention provides a tissue puncture closure assembly, the assembly comprising a tissue puncture closure device having a distal and a proximal end, a block and tackle disposed in the tissue puncture closure device and anchored to the proximal end, a first filament extending from the block and tackle, an anchor attached to the first filament at the distal end of the tissue puncture closure device, and a sealing plug attached to the first filament between the anchor and the block and tackle.

Another embodiment of the present invention comprises an Angio-Seal® device including a block and tackle configured to generate a mechanical advantage and compress a collagen sponge and anchor together across an arteriotomy. The block and tackle may be any device that functions in a pulley-like manner to trade force for distance, although it may or may not include any actual rolling pulleys. One embodiment of the block and tackle includes an elongated device having three holes and two risers. The first hole may be separated from the second and third holes by the risers. The risers prevent interference between filament loops that extend through the first and second holes of the block and tackle. In order to create the mechanical advantage, the filament is looped through the block and tackle multiple times. The third hole may be used for securing a separate filament between the block and tackle component and the collagen sponge and anchor. The separate filament extending from the block and tackle to the collagen sponge and anchor is configured such that an outward or proximal force on the filament threaded through the block will result in a compression force between the anchor and collagen sponge.

An additional embodiment of the present invention is directed to a method of sealing a tissue puncture accessible through a percutaneous incision. First, an internal component and an external component are inserted into the incision. The internal component is passed through the puncture, into a lumen, and positioned against an interior wall of the lumen. The external component is positioned outside of the lumen, adjacent to an exterior wall of the puncture. Second, an initial outward or proximal force is applied to a device that translates the initial outward force into a multiplied compression force between the internal component and external component across the puncture. The initial outward force is multiplied into a compression force by a block and tackle according to some embodiments to provide a mechanical advantage. Third, any non-biologically resorbable portions of the device are removed from the incision, leaving the internal component and external component across the puncture.

The present invention contains numerous advantages over the prior art. The prior art methods of sealing an internal incision require a separate tamping step and the application of sustained compression pressure on the internal and external components for a period of time in order to seal the puncture. The compression pressure requires either a manual force or the use of a special spring. The present invention provides a method and apparatus for multiplying a compression force between the internal and external components through a mechanical advantage. The compression force generated by the described device does not require a prolonged period of manual or spring-compression, and therefore eliminates the extra steps and/or components required by the prior art.

The foregoing, together with other features and advantages of the present invention, will become more apparent when referred to the following specification, claims and accompanying drawings.

BRIEF DESCRIPTION OF THE DRAWINGS

Preferred embodiments of the invention are described below with reference to the accompanying drawings.

Throughout the drawings, identical reference numbers represent similar, but not necessarily identical, elements.

DETAILED DESCRIPTION OF THE INVENTION

Reference is now be made to the drawings to describe presently preferred embodiments of the invention. It is to be understood that the drawings are diagrammatic and schematic representations of the presently preferred embodiments, and are not limiting of the present invention, nor are they necessarily drawn to scale.

The present invention is directed to a tissue puncture closure assembly including a closure or sealing device incorporating a block and tackle for assisting in sealing a puncture, such as a vascular puncture, through a percutaneous incision. The sealing device includes an internal and an external component. The block and tackle creates a mechanical advantage by translating a proximal or outward force into a multiplied compression force between the internal and external sealing components. The sealing device may be incorporated with an Angio-Seal® device. The internal and external components are preferably an anchor and collagen sponge respectively. Likewise, the vascular puncture is generally an arteriotomy intentionally created in order to perform a vascular procedure. The ability to exert a multiplied compression force across the arteriotomy eliminates additional steps of tamping the collagen sponge with a tamping tube, attaching a tamping spring to a filament in order to exert a continuous pressure between the anchor and collagen sponge, and later removing the spring from the filament. Also, while embodiments of the present invention are described in the context of a method and apparatus for generating a mechanical advantage with a specifically illustrated puncture closure device, it will be appreciated that the teachings of the present invention are applicable to other devices and applications as well. For example, the block and tackle may be incorporated into other types of medical devices that require a pulling force to compress or cinch various members together.

Figure 1:
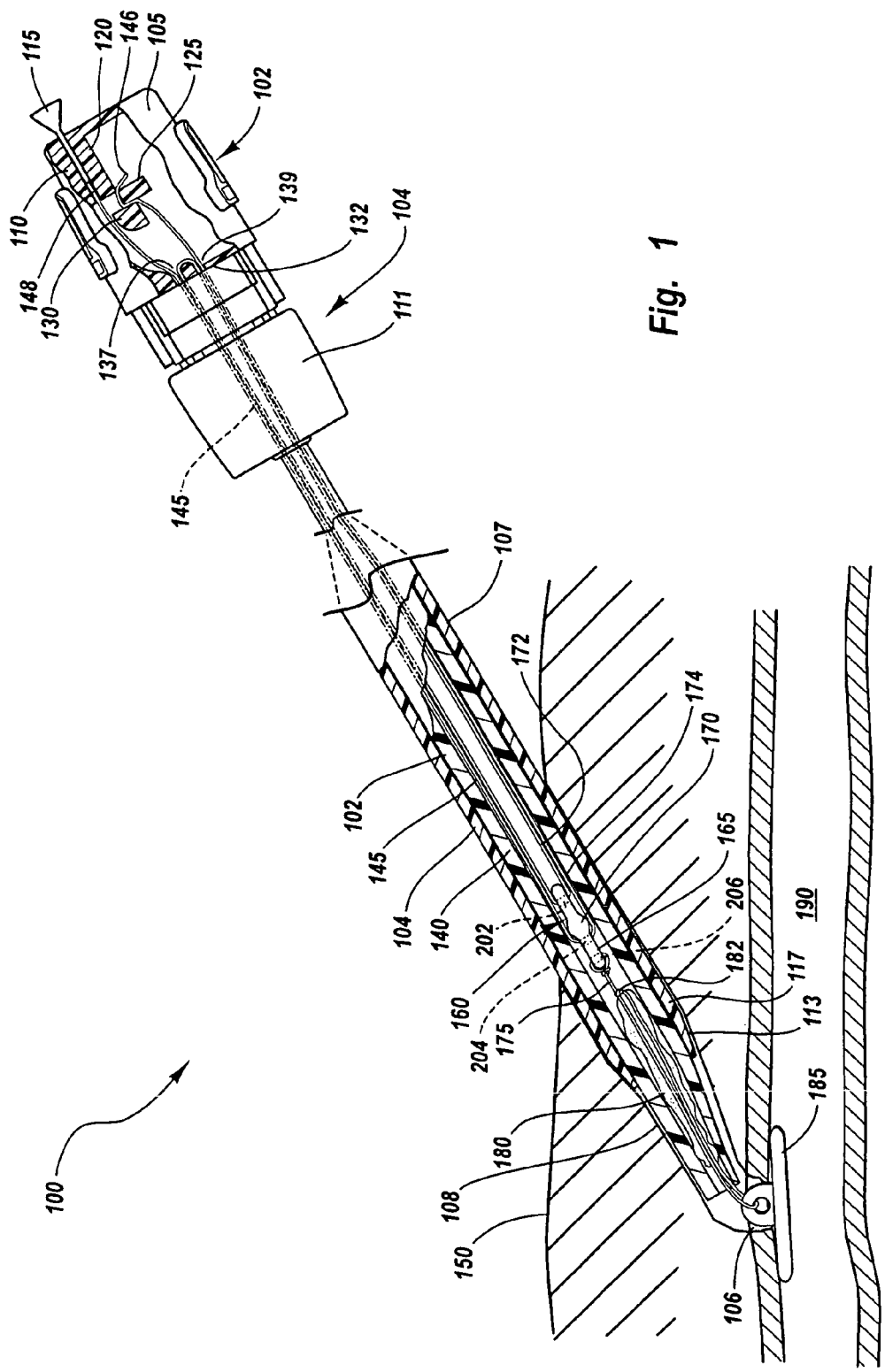
FIG. 1 is a cutaway perspective view of a tissue puncture closure assembly including a block and tackle according to one embodiment of the present invention.

Reference is initially made to FIG. 1, which illustrates a cutaway perspective view of a tissue puncture closure assembly, designated generally as 100. The tissue puncture closure assembly 100 includes a closure device 102 and an insertion sheath 104. FIG. 1 illustrates the closure device 102 positioned with an anchor 185 set against an internal wall of a lumen, which is an artery 190 according to FIG. 1. A puncture or hole 106 in which the anchor 185 enters the artery 190 is referred to as an arteriotomy. One or more steps are performed to insert the closure device 102 through an incision 108 in a patent's skin 150 and properly set the anchor 185 as shown. One example of the steps is described in more detail in referenced U.S. Pat. Nos. 5,662,681 and 5,282,827.

The closure device 102 further includes a first filament 175, a cap 105, a second filament 145 threaded through a plate 165 and the cap 105 to create a block and tackle 160, a sleeve 140, a collagen sponge 180, and an anchor 185. The cap 105 is located at a proximal end of the closure device 102. The second filament 145 is fixed to the cap 105. The second filament 145 extends from a first end 146, to the plate 165, and back through the cap 105, where it terminates with an optional tab 115. The second filament 145 is separate and distinct from the first filament 175.

The sleeve 140 is a hollow tubular member that extends distally from the cap 105 to the collagen sponge 180 and anchor 185 located at a distal end of the closure device 102. The block and tackle 160 is partially disposed within the sleeve 140 between a proximal end 122 of the cap 105 and the collagen sponge 180. The first filament 175 loops through the block and tackle 160 and extends through the collagen sponge 180 and around the anchor 185, then returns proximally through or around the sponge 180 and ties onto itself in a self-tightening slipknot 182 between the collagen sponge 180 and the block and tackle 160. Thus, as tension is applied to the first filament 175 via the block and tackle 160, the knot 182 slips along the first filament 175 distally, cinching the collagen sponge 180 and compressing the anchor 185 and the collagen sponge 180 together across the puncture 106.

The cap 105 is a semi-hollow rigid structure comprised of lightweight plastic or another material. A first end 146 of the second filament 145 is fixably secured to the cap 105 with first and second stop plugs 125, 130. First and second recesses 137, 139 are also disposed at a distal end of the cap 105 so as to allow portions of the second filament 145 to pass between the cap 105 and the plate 165. Edges 132 of the first and second recess 137, 139 may be beveled or rounded to minimize friction as the second filament 145 passes between the cap 105 and the plate 165. Extending outside the cap 105 is the tab 115 attached to the second filament 145, which provides a grip for an operator to apply a proximal or outward force to the second filament 145. The tab 115 is attached to a second end 148 of the second filament 145 opposite from the first end 146 that is fixably secured by the first and second stop plugs 125, 130. The first and second stop plugs 125, 130 are rigid members compressed together around the second filament 145 such that the second filament 145 cannot slide therebetween. A portion of the second filament 145 extends from the plate 165 through the first recess 137, through first and second silicone tensioners 110, 120 and out to the tab 115. The first and second tensioners 110, 120 impart a frictional force to portions of the second filament 145 passing therethrough so as to prevent the tab 115 from accidentally being pulled at an improper time. The operation of compressing the anchor 185 and collagen sponge 180 is described below with reference to FIGS. 3A-3D.

As described above, the block and tackle 160 is located at least partially within the sleeve 140. The block and tackle 160 comprises a plate 165 having a plurality of holes therein, the cap 105 (including the holes 137, 139 disposed therein), and the second filament 145 traversing the plate 165 and the cap 105. According to the embodiment of FIG. 1, the plate 165 includes three holes 202, 204, 206. At least two of the holes 202, 204 facilitate looping of the second filament 145 and therefore provide a mechanical advantage to the operator in generating tension in the first filament 175. Alternatively, fewer or additional holes may be incorporated into the plate 165 and the cap 105 in order to generate a different mechanical advantage. The plate 165 is shaped to fit within the confines of the sleeve 140. It may be desirable to minimize the diameter of the sleeve 140 and a profile of the plate 165 in order to minimize the size of incision(s) that must be made in a patient. The diameter of the sleeve 140 is not drawn to scale in FIG. 1 but is exaggerated to illustrate the components of the tissue puncture closure assembly 100. The plate 165 may include one or more riser portions, for example the two riser portions 170 shown. The two riser portions 170 protrude so as to minimize interference between first and second loops 172, 174 of the second filament 145 comprising the block and tackle 160. The shape and structure of the plate 165 is described in more detail below with reference to FIGS. 2A and 2B.

The second filament 145 traverses the plate 165 to the cap 105 in a manner that provides a mechanical advantage when an outward or proximal force is applied to the second filament 145. As mentioned above, the first end 146 of the second filament 145 is fixably secured to the cap 105 via the first and second stop plugs 125, 130. The second filament 145 extends from the first end 146 through the second recess 139 of the cap 105 and through the first hole 202 in the plate 165. The second filament 145 then returns proximally and loops through the first and second recess 137, 139, respectively, of the cap 105. The second filament 145 extends distally through the second recess 139 and through a second hole 204 in the block 160. The second filament 145 then returns back through the first recess 137 of the cap 105, between first and second silicone tensioners 110, 120 and out the proximal end 122 of the cap 105, terminating with the tab 115. By looping the second filament 145 multiple times between the cap 105 and the plate 165, a four to one (4:1) mechanical advantage is created on the plate 165. The mechanical advantage of the block and tackle 160 thus multiplies an initial manual force when applied proximally via the tab 115. Therefore, in the illustrated embodiment, when the tab 115 is pulled proximally or away from the cap 105 with an initial outward force, the second filament 145 traverses the plate 165 and cap 105, generating a force on the plate 165 and therefore the first filament 175 of approximately four times the initial outward force placed on the tab 15.

The first filament 175 connects the block and tackle 160 to the collagen sponge 180 and anchor 185. The first filament 175, collagen sponge 180, and anchor 185 may be biologically resorbable, as they will generally be left in the patient's body after the puncture 106 is sealed. The first filament 175 loops through the third hole 206 in the plate 165 and knots onto itself in the one-way slip knot 182. The first filament 175 also passes through the collagen sponge 180, the anchor 185, and back through the collagen sponge 180 where it is slip-knotted between the sponge 180 and the plate 165. Therefore, the one-way slip knot 182 tightens and moves distally toward the anchor 185 when under sufficient tension, and compresses the collagen sponge 180 and the anchor 185 together, but does not retract proximally or release the compression between the anchor 185 and sponge 180 when tension is released. By extending the first filament 175 through the collagen sponge 180 and anchor 185 as described above with the slip-knot 182, a single outward or proximal tension force on the first filament 175 will cause the collagen sponge 180 and anchor 185 to compress together across the arteriotomy 106 in the artery 190. Since the first filament 175 is attached to the block and tackle 160, the outward force generated on the block and tackle 160 via the second filament 145 is translated into a compression force between the collagen sponge 180 and anchor 185.

The closure device 102 is shown in FIG. 1 engaged with the insertion sheath 104. The insertion sheath 104 comprises a generally flexible tubular member 107 with a hemostatic valve 111 at a proximal end thereof. The insertion sheath 104 includes a fold 113 disposed at a first or distal end 117 thereof. The fold 113 acts as a one-way valve to the anchor 185. The fold 113 is a plastic deformation in a portion of the insertion sheath 104 that elastically flexes as the anchor 185 is pushed out through the first end 117 of the insertion sheath 104. The anchor is initially arranged in a low profile configuration aligned a longitudinal axis of the insertion sheath 104. However, as the anchor 185 passes though and out of the first end 117 of the insertion sheath 104, the fold 113 springs back and closes, such that the anchor may not be reinserted into the insertion sheath 104. Further, as the closure device 102 is retracted with respect to the insertion sheath 104, the anchor is automatically rotated into a transverse expanded configuration as shown in FIG. 1, deployed against the internal wall of the artery 190.

Figure 2A:
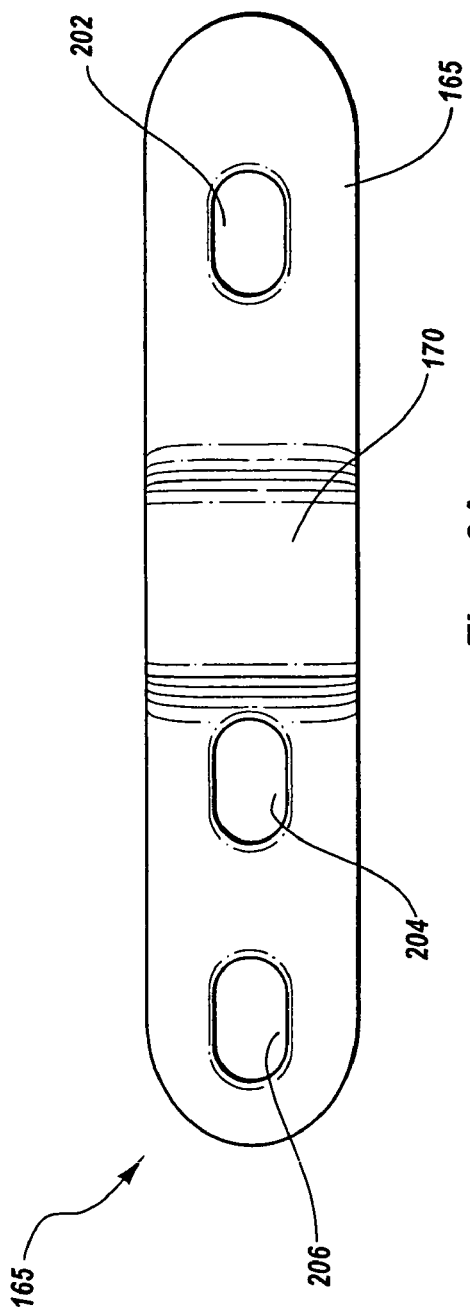
FIG. 2A is a top view of the block and tackle illustrated in FIG. 1.
Figure 2B:
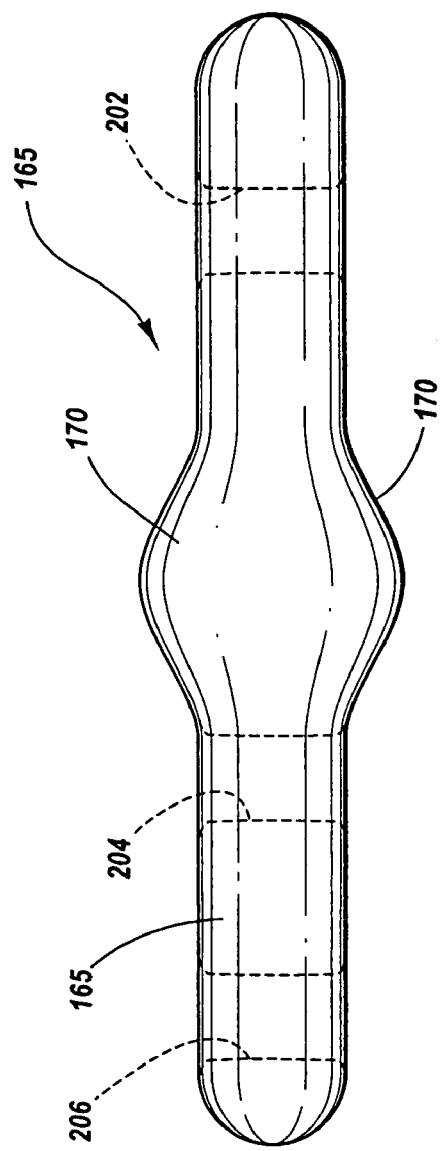
FIG. 2B is a profile view of the block and tackle component illustrated in FIG. 1.

Reference is next made to FIGS. 2A and 2B, which illustrate detailed views of the plate 165. FIG. 2A is a top view of one embodiment of the plate 165. The plate 165 includes opposing risers 170, the first hole 202, the second hole 204, and the third hole 206. The plate 165 is a rigid or semi-rigid elongated member. The plate 165 may or may not be made of biologically resorbable materials. The first hole 202 is positioned at a first or proximal end of the plate 165. The second and third holes 204, 206 are positioned distal to the first hole 202. The risers 170 are shown positioned between the first and second holes 202, 204 and are mirror images of one another, but this is not necessarily so. According to some embodiments there may be only one riser 170, and according to others there may be no risers at all. Still other embodiments may include three or more risers 170. Further, the two risers 170 shown (or others) need not be the same size or shape, and may or may not be located directly opposite of one another as shown. However, according the embodiment of FIGS. 2A-2B, a suture may be looped through both the first and second holes 202, 204 with little or no interference therebetween because of the spacing between loops afforded by the risers 170. If the filament loops 172, 174 (FIG. 1) are allowed to interfere with one another, there is a potential for tangles or obstructions that the risers 170 help to avoid.

The third hole 206 is positioned at a distal end of the plate 165. The third hole 206 may be used to attach the plate 165 to the anchor 185 and collagen sponge 180 via the first filament 175 as illustrated in FIG. 1.

FIG. 2B is a profile view of the plate 165. FIG. 1 also illustrates a profile view of the plate 165 showing how it is positioned relative to the tissue puncture closure assembly 100. The profile view clearly illustrates the two risers 170 on opposing sides of the plate 165. The first, second, and third holes 202, 204, 206 are phantomly illustrated to show how the holes extend through the plate 165.

Reference is next made to FIGS. 3A-3D to illustrate the process of compressing the collagen sponge and anchor together with the aid of the block and tackle 160. These figures also illustrate removal of the non-biologically resorbable portions of the tissue puncture closure assembly 100 from a patient. The process described below is focused on the compression of the collagen sponge 180 and anchor 185 so as to emphasize the particular points of the present invention. However, numerous other steps may be required to initially insert the tissue puncture closure assembly 100 into a patient and properly position the collagen Sponge 180 and anchor 185 to seal the puncture 106. Such steps may include puncturing the vessel 190 and threading a guide wire (not shown) into the vessel 190. The insertion sheath 104 and a locator may then be threaded over the guide wire until the insertion sheath 104 has penetrated the vessel. The guide wire and locator may then be removed, leaving the insertion sheath 104, through which tools such as the vascular closure device 102 may be delivered to the vascular puncture site.

Figure 3A:
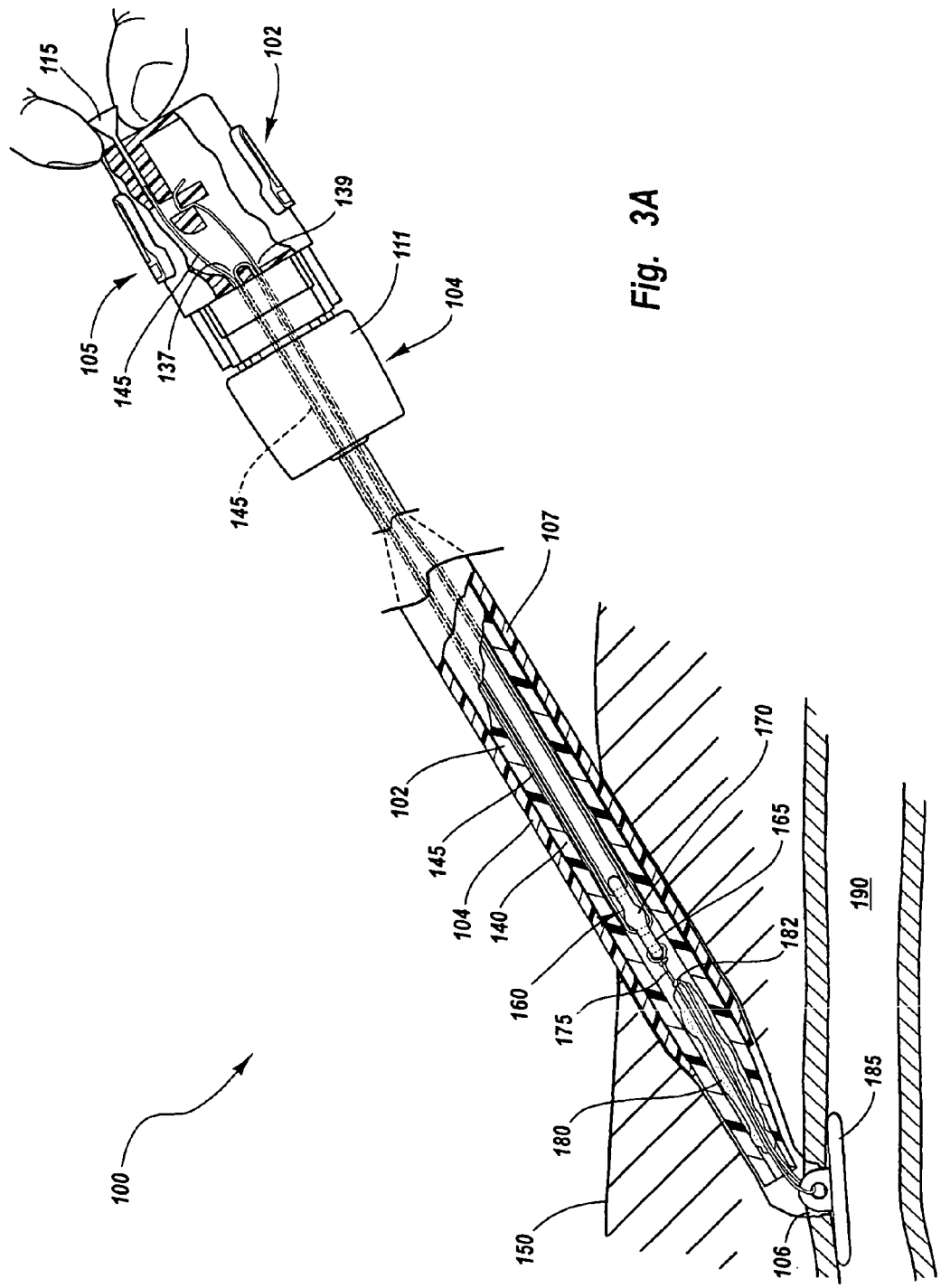
FIG. 3A is a cross-sectional view of a tissue puncture closure assembly including a block and tackle, after an anchor and collagen sponge have been properly positioned within an incision according to one embodiment of the present invention.
Figure 3B:
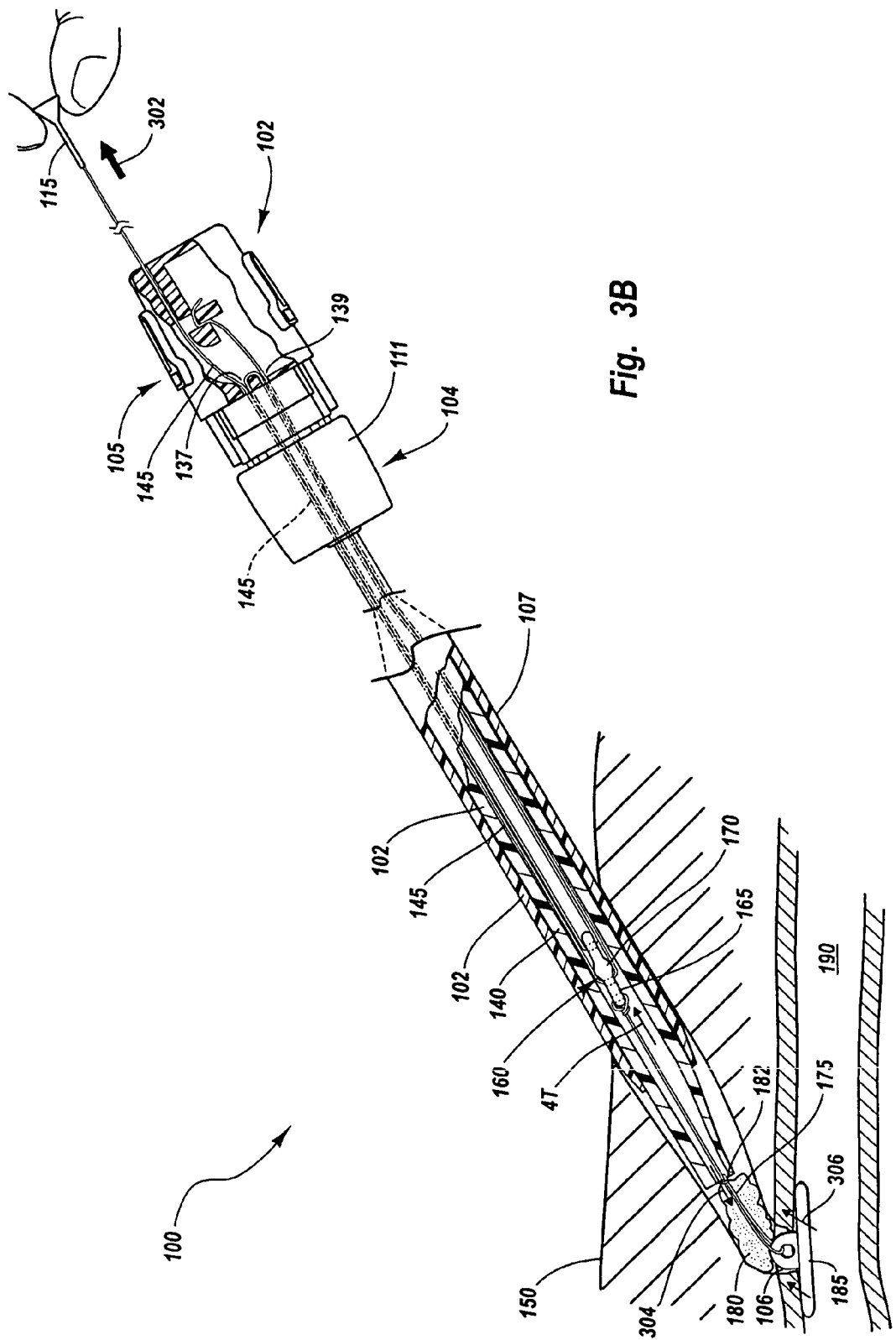
FIG. 3B is a cross-sectional view of the tissue puncture closure assembly including the block and tackle of FIG. 3A, illustrating a result of a generated compression force between the anchor and collagen sponge in response to pulling a tab.

FIG. 3A is a cross-sectional view of the tissue puncture closure assembly 100 including one preferred embodiment of the block and tackle 160 following deployment of the anchor 185 and collagen sponge 180, but prior to sandwiching the puncture 106 by compressing the anchor 185 and the collagen sponge 180 together. FIG. 3A represents the same situation illustrated in FIG. 1. FIG. 3B is a cross-sectional view of the tissue puncture closure assembly 100 including the embodiment of the block and tackle component 160 shown in FIG. 3A. FIG. 3B illustrates the generated tension in the first and second filaments 175, 145 by a force applied to the tab 115 in the direction of arrow 302. As an outward force of 1 T is applied to the second filament 145 in the direction of the arrow 302, the block and tackle 160 applies a force of 4 T to first filament 175. The tension in the first filament 175 causes the slipknot 182 to slide and compress the collagen sponge 180 and the anchor 185 together. Compression forces (represented by a pair of arrow 304, 306) across the puncture 106 results in hemostasis. The additional force generated by the block and tackle 160 and the one-way slip knot 182 hold the collagen sponge 180 and anchor 185 together such that manual or spring pressure does not need to be applied in order to produce reliable hemostasis.

Figure 3C:
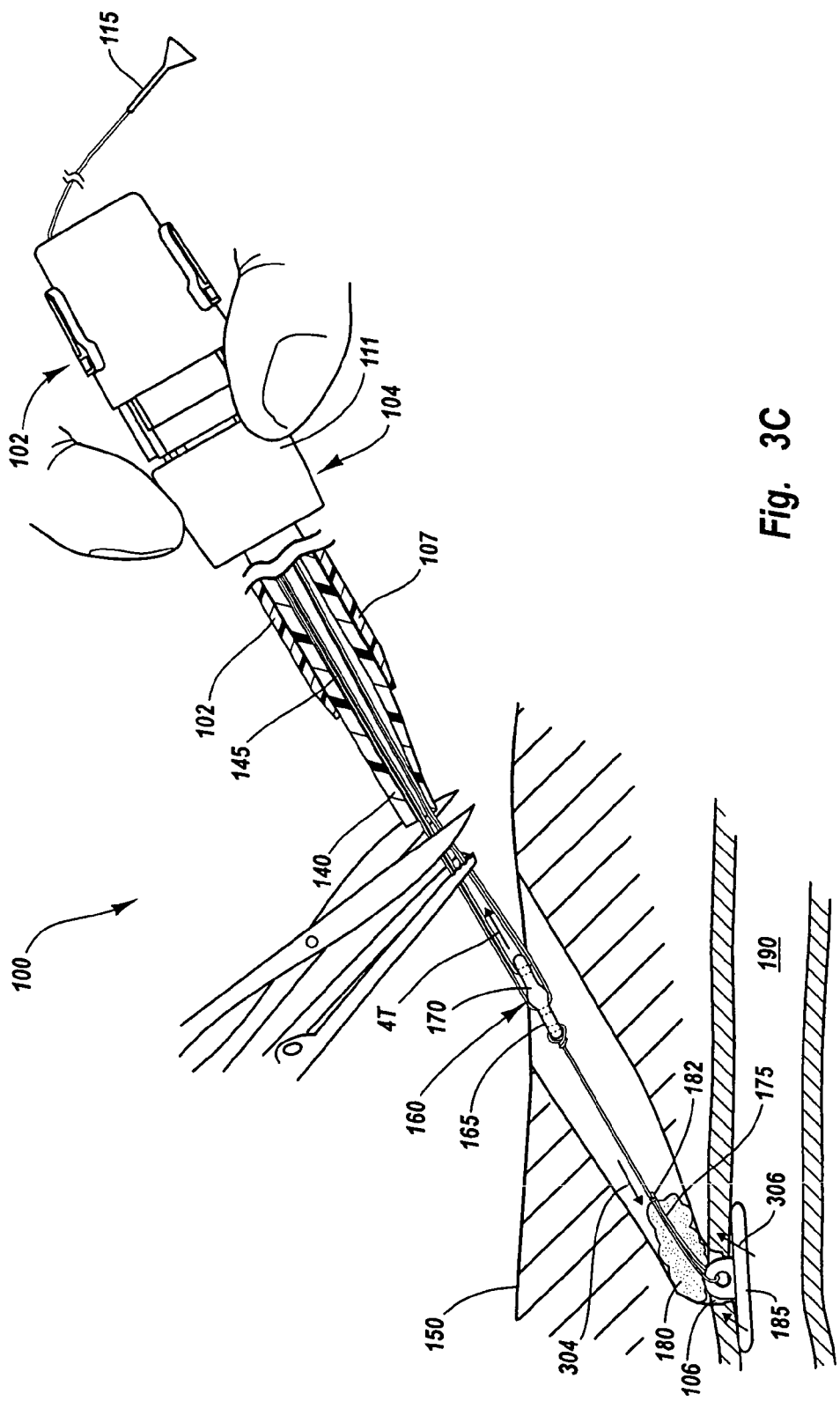
FIG. 3C is a cross-sectional view of the tissue puncture closure assembly including the block and tackle of FIG. 3B, illustrating removal and separation of the tissue puncture closure device from the anchor and sponge.
Figure 3D:
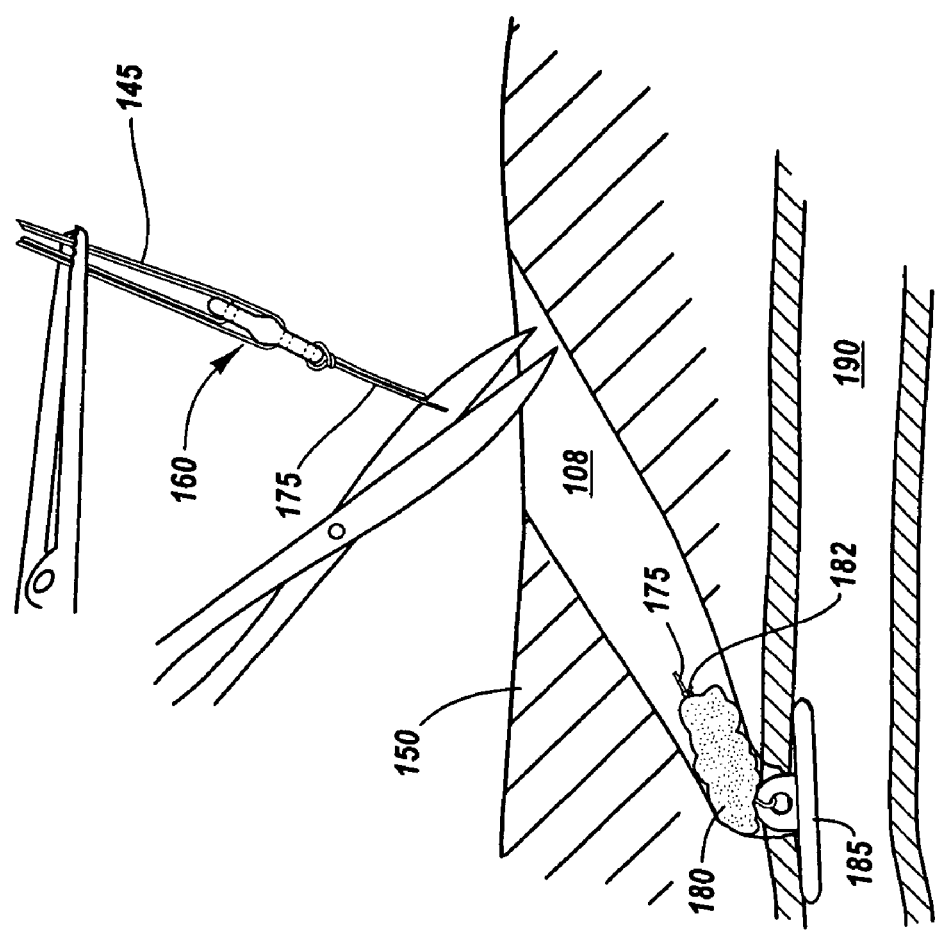
FIG. 3D is a cross-sectional view of the tissue puncture closure assembly illustrating final removal of the block and tackle of FIG. 3C.

FIGS. 3C-3D are a cross-sectional views of the tissue puncture sealing assembly 100 including the embodiment of the block and tackle 160 shown in FIG. 3B and illustrating the removal and separation of a portion of the closure device 102 from the incision 108. After the anchor 185 and the collagen sponge 180 have been compressed together across the puncture 106, all of the puncture closure assembly 100 components are removed from the patient, except for the anchor 185, the collagen sponge 180, and the first filament 175. To remove the tissue puncture closure assembly 100 (except for the components mentioned above), the first filament 175 may be cut proximal to the knot 182, and the closure device 102 and insertion sheath 104 are pulled away from the patient as shown in FIG. 3D. Alternatively, the plate 165 may remain in the incision 108 and the second filament 145 may be cut one or more times, followed by removing the cap 105, the sleeve 140, and the insertion sheath 102 as shown in FIG. 3C. Further, any remaining segments of the second filament 145 may be withdrawn from the incision 108, or left in the incision if the second filament 145 comprises biologically resorbable materials.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A tissue puncture closure assembly, comprising:
   a closure device having a distal and a proximal end;
   a block and tackle disposed in the closure device, a portion of the block and tackle being anchored to the proximal end;
   a first filament extending from a distal end of the block and tackle;
   an anchor attached to the first filament at the distal end of the closure device;
   a sealing plug attached to the first filament between the anchor and the block and tackle;
   wherein the block and tackle is configured to provide a mechanical advantage to move the sealing plug and the anchor together when the anchor is held in a fixed position, wherein the mechanical advantage comprises a ratio greater than 1:1 between an output force used to move the sealing plug and the anchor together and an input force applied to the closure device, wherein the block and tackle is spaced proximally of the anchor and the sealing plug, and the tackle comprises a continuous second filament that is separate and distinct from the first filament.

2. The tissue puncture closure assembly according to claim 1 wherein the block and tackle comprises:
   a plate having a plurality of holes disposed therein;
   the second filament anchored to the proximal end of the closure device and looping through at least two of the plurality of holes.

3. The tissue puncture closure assembly according to claim 2 wherein the second filament terminates with a pull-tab extending from the proximal end of the tissue puncture closure device.

4. The tissue puncture closure assembly according to claim 2 wherein the plate further comprises at least two risers to space the second filament looping through the plurality of holes.

5. The tissue puncture closure assembly according to claim 2 wherein the first filament is slidingly attached to the anchor and the sealing plug.

6. The tissue puncture closure assembly according to claim 5 wherein the first filament extends distally from the block and tackle through the sealing plug and the anchor, back proximally toward the block and tackle, and is tied onto itself in a slip knot disposed between the block and tackle and the sealing plug.

7. The tissue puncture closure assembly according to claim 2 wherein the plurality of holes comprises three holes.

8. The tissue puncture closure assembly according to claim 1 wherein the first filament, the sealing plug, and the anchor are biologically resorbable.

9. The tissue puncture closure assembly according to claim 1, further comprising an insertion sheath receptive of the closure device, the insertion sheath comprising a flexible tube with a hemostatic valve at a proximal end and a one-way anchor valve at a distal end.

10. The tissue puncture closure assembly according to claim 9 wherein the one-way anchor valve comprises a fold in the distal end of the flexible tube.

11. An internal incision sealing device comprising:
an internal component configured to be positioned against an internal portion of an incision;
an external component configured to be positioned at an external portion of the incision, wherein the external component is attached to the internal component by a first slip-knotted filament such that tension on the first filament compresses the internal component and external component together; and
a block and tackle disposed within the internal incision sealing device and operatively connected to the internal and external components with the first filament, the first filament extending from a distal end of the block and tackle, the block and tackle being configured to provide a mechanical advantage to move the internal and external components together when the internal component is positioned against the internal portion of the incision, wherein the mechanical advantage comprises a ratio greater than 1:1 between an output force used to move the internal and external components together and an input force applied to the device, wherein the block and tackle is positioned proximally of the internal and external components, and the tackle comprises a continuous second filament that is separate and distinct from the first filament.

12. An internal incision sealing device according to claim 11, wherein the mechanical advantage causes the slip knot to slide and compress the internal and external components together across the incision.

13. An internal incision sealing device according to claim 11, wherein the internal incision is an arteriotomy.

14. An internal incision sealing device according to claim 11, wherein the second filament is fixed to a cap of the sealing device at a first end, and free at a second end.

15. An internal incision sealing device according to claim 14 wherein the second end further comprises a pull-tab.

16. An internal incision sealing device according to claim 14 wherein the block and tackle comprises at least two loops of the second filament, creating at least a four to one mechanical advantage.

17. An internal incision sealing device according to claim 14, wherein the second filament is fixed to the cap with at least one stop plug.

18. An internal incision sealing device according to claim 11, wherein the internal component is an anchor shaped to advance in a low profile configuration through an insertion sheath, and automatically rotate into an expanded configuration upon exit from the insertion sheath and retraction of the sealing device.

19. An internal incision sealing device according to claim 11, wherein the external component is a collagen sponge.

20. An internal incision sealing device according to claim 11, wherein the internal component, the external component, and the first slip-knotted filament are biologically resorbable.

21. An internal incision sealing device according to claim 11, wherein the first slip-knotted filament is attached or looped through the block and tackle, and threads through the external component, through a hole in the internal component, and is knotted proximal of the external component.

22. An internal incision sealing device according to claim 11, wherein the block and tackle comprises a plate with at least two holes extending through.

23. An internal incision sealing device according to claim 22, wherein the plate has at least two riser portions to prevent interference between loops of the second filament.

24. An arteriotomy sealing device, comprising:
an anchor shaped to advance in a low profile configuration and rotate into an expanded configuration when retracted;
a collagen sponge connected in a loop to the anchor by a biologically resorbable filament;
wherein tension on the biologically resorbable filament compresses the collagen sponge and the anchor together; and
a block and tackle positioned proximally of the anchor and the collagen sponge, and operatively connected at a distal end thereof to the biologically resorbable filament for generating a mechanical advantage when the anchor is held in a fixed position, wherein the mechanical advantage comprises a ratio greater than 1:1 between an output force used to move the collagen sponge and the anchor together and an input force applied to the device, wherein the tackle comprises a continuous second filament that is separate and distinct from the biologically resorbable filament.

25. An arteriotomy sealing device according to claim 24 wherein the block and tackle is attached to a cap of the sealing device via the second filament.

26. An arteriotomy sealing device according to claim 25 wherein the second filament is fixably secured to the cap, loops between the block and the cap at least once to create a pair of parallel lengths of the second filament, and extends out of the cap.

27. An arteriotomy sealing device according to claim 24 wherein the block and tackle comprises a plate with at least two holes extending through.

28. An arteriotomy sealing device according to claim 27, wherein the plate has at least two riser portions to prevent interference between filament loops extending through the block.

29. A tissue puncture closure device comprising:
an anchor and a sealing plug coupled together with a first filament;
a block and tackle, the first filament connecting a distal portion of the block and tackle to the anchor and the sealing plug, the block and tackle being configured to provide a mechanical advantage to move the anchor and the sealing plug together when the anchor is held in a fixed position, wherein the mechanical advantage comprises a ratio greater than 1:1 between an output force used to move the anchor and the sealing plug together and an input force applied to the device, wherein the block and tackle is positioned proximally of the anchor and the sealing plug, and the tackle comprises a continuous second filament that is separate and distinct from the first filament.

30. The tissue puncture closure device according to claim 29 wherein the second filament that extends multiple times between a proximal end of the tissue puncture closure device and a longitudinally movable plate.

31. The tissue puncture closure device according to claim 30 wherein the second filament is configured to be pulled by a user to move the anchor and the sealing plug together.

32. The tissue puncture closure device according to claim 30 wherein the movable plate moves toward the proximal end of the tissue puncture closure device when the second filament is pulled.

33. The tissue puncture closure device according to claim 30 wherein the first filament couples the movable plate to the anchor and the sealing device.

34. The tissue puncture closure device according to claim 29 wherein the sealing plug and the anchor are biologically resorbable.

35. A tissue puncture closure assembly, comprising:
- a closure device having a distal and a proximal end;
- a block and tackle disposed in the closure device, a portion of the block and tackle being anchored to the proximal end;
- a first filament extending from a distal end of the block and tackle;
- an anchor attached to the first filament at the distal end of the tissue puncture closure device;
- a sealing plug attached to the first filament between the anchor and the block and tackle;
- wherein the block and tackle is configured to provide a mechanical advantage to move the sealing plug and the anchor together when the anchor is held in a fixed position, wherein the mechanical advantage comprises a ratio greater than 1:1 between an output force used to move the sealing plug and the anchor together and an input force applied to the closure device, wherein the block and tackle is spaced proximally of the anchor and the sealing plug;
- wherein the block and tackle includes a second filament, the second filament being separate and distinct from the first filament and having at least two length portions arranged side-by-side.

* * * * *